(12) United States Patent
Vahala et al.

(10) Patent No.: US 8,725,232 B2
(45) Date of Patent: May 13, 2014

(54) THERAPEUTIC APPARATUS (75) Inventors: Erkki Tapani Vahala, Hyvinkaa (FI);
Shunmugavelu Sokka, Cambridge, MA (US); Julius Koskela, Helsinki (FI);
Max Oskar Kohler, Espoo (FI)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/519,145

(22) PCT Filed: Dec. 21, 2010

(86) PCT No.: PCT/IB2010/055976
§ 371 (c)(1),
(2), (4) Date: Jun. 26, 2012

(87) PCT Pub. No.: WO2011/080664
PCT Pub. Date: Jul. 7, 2011

(65) Prior Publication Data
US 2012/0296197 A1 Nov. 22, 2012

Related U.S. Application Data (60) Provisional application No. 61/290,265, filed on Dec. 28, 2009.

(51) Int. Cl.
A61B 5/055 (2006.01)
A61B 8/00 (2006.01)
A61H 1/00 (2006.01)
A61B 18/04 (2006.01)
A61F 7/00 (2006.01)

(52) U.S. Cl.
USPC ............... 600/411; 600/439; 601/2; 606/27; 607/96

(58) Field of Classification Search
USPC .......... 600/410, 411, 424, 439, 447; 601/2, 3; 606/27; 607/96
See application file for complete search history.

(56) References Cited

U.S. PATENT DOCUMENTS 5,806,521 A 9/1998 Morimoto et al.
7,302,286 B2 11/2007 Camus et al.
(Continued)

FOREIGN PATENT DOCUMENTS

WO 0243804 A1 6/2002
WO 2006018686 A1 2/2006
(Continued)

OTHER PUBLICATIONS

Bhattarai, Keshav. "High Intensity Focused Ultrasound (HIFU)." American Chronicle. http://www.americanchronicle.com/articles/view/117740. Sep. 6, 2009. Chongqing Medical University, China.
(Continued)

Primary Examiner — Michael Rozanski (57) ABSTRACT

A therapeutic apparatus comprising a high intensity focused ultrasound system (302) for sonicating a sonication volume (324) of a subject (320). The therapeutic apparatus further comprises a magnetic resonance imaging system (300) for acquiring magnetic resonance thermometry data (350) within an imaging volume (316). The sonication volume is within the imaging volume. The therapeutic apparatus further comprises a controller (304) for controlling the therapeutic apparatus. The treatment plan comprises instructions for controlling the operation of the high intensity focused ultrasound system. The controller is adapted for sonicating (100) the target volume using the high intensity focused ultrasound system. The controller is adapted for repeatedly acquiring (102) magnetic resonance thermometry data using the magnetic resonance imaging system during execution of the treatment plan. The controller is adapted for modifying (104) the treatment plan during execution of the treatment plan using the magnetic resonance thermometry data.

18 Claims, 3 Drawing Sheets

(56) References Cited

U.S. PATENT DOCUMENTS

| | | | |
|---|---|---|---|
| 7,520,856 B2 | 4/2009 | Vaezy et al. | |
| 2006/0206105 A1 | 9/2006 | Chopra et al. | |
| 2007/0232912 A1 | 10/2007 | Chen et al. | |
| 2008/0319375 A1 | 12/2008 | Hardy | |
| 2009/0054772 A1 | 2/2009 | Lin et al. | |
| 2009/0088623 A1 | 4/2009 | Vortman et al. | |
| 2009/0234175 A1 | 9/2009 | Maier | |
| 2012/0035464 A1* | 2/2012 | Raju et al. | 600/411 |

FOREIGN PATENT DOCUMENTS

| | | | |
|---|---|---|---|
| WO | 2007114917 | A2 | 10/2007 |
| WO | 2008120117 | A2 | 10/2008 |
| WO | 2010122449 | A1 | 10/2010 |
| WO | 2010140125 | A1 | 12/2010 |

OTHER PUBLICATIONS

Le Floch, Vincent et al. "Ultrasound Simulation in the Distal Radius Using Clinical High-Resolution Peripheral-CT Images." National Institute of Health. Ultrasound Med Biol. Aug. 2008; 34(8): 1317-1326, US.

Foxchase Cancer Center. "Treatment Planning." . http://www.fccc.edu/patients/preparingProcedures/ radiationTherapy/treatmentPlanning/index.html. 2006. Philadelphia, PA.

Guenther, Drake et al. "A Method for Accurate in Silico Modeling of Ultrasound Transducer Arrays." Department of Biomedical Engineering, University of Virginia, US. Ultrasonics 49 (2009) 404-412.

The Haifu System. Ultrasound Therapeutics Ltd. Main Parameters of the Haifu System. http://www.utlltd.co.uk/index.php?option=com_content&task=view&id=29&Itemid=117. 2006. UK.

Jolesz, Ferenc A. "MRI-Guided Focused Ultrasound Surgery." The Annual Review of Medicine. 60:417-30. 2009. Boston, MA.

Rata, Mihaela et al. "Optimization of the Thermal Dosimetry for Endocavitary HICU Ablation of Sectorial Digestive Tumours." International Symposium on Therapeutic Ultrasound. American Institute of Physics Conf. Proc.—May 21, 2007—vol. 911, pp. 278-282.

Shen, Feimo, PhD. et al. Three-Dimensional Sonography With Needle Tracking. Role in Diagnosis and Treatment of Prostate Cancer. Journal of Ultrasound in Medicine. Jun. 1, 2008. vol. 27 No. 6, pp. 895-905. California, US.

Urban, Nicole et al. "Use of a Stochastic Simulation Model to Identify an Efficient Protocol for Ovarian Cancer Screening." U.S. National Library of Medicine. 1997. Seattle, WA, US.

* cited by examiner

THERAPEUTIC APPARATUS

This application is a national stage application under 35 U.S.C. §371 of International Application No. PCT/Ib2010/055976 filed on Dec. 21, 2010 and published in the English language on Jul.7, 2011 as International Publication No. WO/2011/0806K which claims priority to U.S. Application No. 61/290,265 filed on Dec. 28, 2009, the entire disclosures of which are incorporated herein by reference.

TECHNICAL FIELD

This invention relates to high intensity focused ultrasound, in particular to high intensity focused ultrasound guided by magnetic resonance imaging.

BACKGROUND OF THE INVENTION

Ultrasound from a focused ultrasonic transducer can be used to selectively treat regions within the interior of the body. Ultrasonic waves are transmitted as high energy mechanical vibrations. These vibrations induce tissue heating as they are damped, and they can also lead to cavitation. Both tissue heating and cavitation can be used to destroy tissue in a clinical setting. However, heating tissue with ultrasound is easier to control than cavitation.

Ultrasonic treatments can be used to ablate tissue and to kill regions of cancer cells selectively. This technique has been applied to the treatment of uterine fibroids, and has reduces the need for hysterectomy procedures. The treatment of a region with ultrasound is referred to as sonication.

To selectively treat tissue, a focused ultrasonic transducer can be used to focus the ultrasound on a particular target volume. The transducer is typically mounted within a medium, such as degassed water, that is able to transmit ultrasound. Actuators are then used to adjust the position of the ultrasonic transducer and thereby adjust the tissue region that is being treated. Medical imaging may be used to guide such ultrasonic therapy. U.S. Patent Application U.S. 2009/0088623 discloses an image guided therapy system comprising an ultrasonic transducer and a magnetic resonance imaging device. The rapid acquisition of temperature-sensitive magnetic resonance images of the patient is disclosed. However, the use of these images to modify the treatment plan during sonication is not disclosed.

SUMMARY OF THE INVENTION

The invention provides for a therapeutic apparatus and a computer program product in the independent claims. Embodiments are given in the dependent claims.

Embodiments of the invention may provide for improved monitoring and control of a high intensity focused ultrasound system by performing magnetic resonance thermometry during sonication. Magnetic resonance thermometry data acquired during the sonication may be used to modify the treatment plan during sonication.

The invention provides for a therapeutic apparatus comprising a high-intensity focused ultrasound system for sonicating a sonication volume of a subject. High-intensity focused ultrasound systems use an ultrasonic transducer to focus or concentrate ultrasonic energy in a sonication volume. The ultrasound energy may be used to heat the sonication volume or to mechanically disrupt tissue or cells or to locally administer drugs through drug-releasing chemical compounds within the sonication volume. For instance the ultrasound may be used to warm tissue or may be used to heat the tissue to a point where necrosis is induced. The ultrasonic energy may also cause mechanical damage to tissue or cells within the sonication volume. For instance at higher intensities bubbles may be formed and mechanical damage due to cavitation of these bubbles may be induced in tissue or cells located within the sonication volume.

The therapeutic apparatus further comprises a magnetic resonance imaging system for acquiring magnetic resonance image data for acquiring magnetic resonance thermometry data from the nuclei of the subject located within an imaging volume. The imaging volume may be considered to be a field of view of the magnetic resonance imaging system. The imaging volume is therefore a volume for which the magnetic field generated by the magnet is sufficiently uniform to acquire magnetic resonance image or magnetic resonance thermometry data. The uniformity of the magnetic field in the imaging volume may be optimized by active shimming coils. The imaging volume may also further defined by a radio frequency transceiver coil which is used to acquire the magnetic resonance imaging data. The radio frequency coil may also be implemented as separate transmit and receive coils.

The sonication volume is within the imaging volume. Magnetic resonance imaging systems use a magnet to align the nuclear spins of nuclei of the subject within the imaging volume. Magnetic field gradients and radio frequency pulses may be used to manipulate the orientation of the spins of these nuclei which are then induced to emit radio frequency signals. These radio frequency signals may be used to extract information from those portions of the subject within the imaging volume. Many magnetic resonance imaging techniques use Fourier transforms. For this reason nuclei outside of the imaging volume are also understood to have an effect on any magnetic resonance data or images. That is to say the nuclei outside of the imaging volume may have an effect on or may contribute to images or data acquired by the magnetic resonance imaging system.

Magnetic resonance image data is defined herein as being the recorded measurements of radio frequency signals emitted by atomic spins by the antenna of a Magnetic resonance apparatus during a magnetic resonance imaging scan. A Magnetic Resonance image is defined herein as being the reconstructed two or three dimensional visualization of anatomic data contained within the magnetic resonance imaging data. This visualization may be performed using a computer.

Magnetic resonance thermometry data is defined herein as being the recorded measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonant frequency.

The therapeutic apparatus further comprises a controller for controlling the therapeutic apparatus. The controller is adapted for receiving a treatment plan specifying a target volume within the imaging volume. In some embodiments, the treatment plan may also specify volumes where energy deposition is to be limited. For instance, in some embodiments the treatment plan may specify volumes which contain critical anatomical structures which could be damaged by sonication. The treatment plan comprises instructions for controlling the operation of the high-intensity focused ultrasound system. The high-intensity focused ultrasound system may have a mechanical apparatus for moving its transducer. The treatment plan may comprise instructions for controlling the mechanical system for moving the transducer of the high-intensity focused ultrasound system. The transducer of the high-intensity focused ultrasound system may also comprise a collection of individual ultrasound transducers. Each of these transducers may be connected to individual power sources which may be used to control the amplitude and phase of these individual ultrasound transducers. Changing the phase and amplitude of the energy applied to these transducers may allow the focusing and direction of the ultrasound beam to different regions within the subject also. The controller is adapted for repeatedly acquiring magnetic resonance thermometry data using the magnetic resonance imaging system during execution of the treatment plan. That is to say that during execution of the treatment plan magnetic resonance thermometry data is repeatedly acquired.

Repeatedly acquiring magnetic resonance thermometry data allows the controller to determine the temperature to which the sonication volume and surrounding tissue is raised during execution of the treatment plan. The controller is adapted for modifying the treatment plan during execution of the treatment plan using the magnetic resonance thermometry data. The controller is able to measure the temperature within the sonication volume and also that of surrounding tissue. This information may be used to modify the treatment plan 'on the fly'. This is advantageous because it allows for a therapeutic apparatus which is able to adjust and optimize the treatment plan based upon the knowledge of current temperatures within the imaging volume and in particular within the sonication volume.

In another embodiment modification of the treatment plan occurs during sonication of the target volume. That is to say that the modification of the treatment plan occurs while ultrasound energy is applied to the transducer of the high-intensity focused ultrasound system. This embodiment is advantageous because it allows the treatment plan to be adjusted based on the current temperature of the target volume and the sonication volume. This may lead to better and more efficient treatments than if the treatment plan were adjusted after a sonication is finished.

In another embodiment, the magnetic resonance imaging system is adapted for acquiring magnetic resonance image data.

In another embodiment the high intensity focused ultrasound system comprises a high intensity focused ultrasound transducer for sonicating the sonication volume.

In another embodiment the magnetic resonance imaging system comprises a magnet adapted for generating a magnetic field for orientating the magnetic spins of nuclei of a subject located within the imaging volume. The magnetic resonance imaging system further comprises a radio frequency coil. The magnetic resonance imaging system further comprises a radio frequency transceiver a radio frequency system adapted for acquiring magnetic resonance data using the radio frequency coil. The magnetic resonance imaging system further comprises a magnetic field gradient coil adapted for spatial encoding of the magnetic spins of nuclei within the imaging volume. The magnetic resonance imaging system further comprises a magnetic field gradient coil power supply adapted for supplying current to the magnetic field gradient coil.

In another embodiment the controller is a computing device comprising a processor. The therapeutic apparatus further comprises a computer-readable storage medium containing instructions for execution by the processor.

A computing device as used herein refers to any device comprising a processor. A processor is an electronic component which is able to execute a program or machine executable instruction. References to the computing device comprising "a processor" should be interpreted as possibly containing more than one processor. The term computing device should also be interpreted to possibly refer to a collection or network of computing devices each comprising a processor. Many programs have their instructions performed by multiple processors that may be within the same computing device or which may even distributed across multiple computing device.

A computer-readable storage medium as used herein is any storage medium which may store instructions which are executable by a processor of a computing device. In some embodiments, a computer-readable storage medium may also be able to store data which is able to be accessed by the processor of the computing device. An example of a computer-readable storage medium include, but are not limited to: a floppy disk, a magnetic hard disk drive, a solid state hard disk, flash memory, a USB thumb drive, Random Access Memory (RAM) memory, Read Only Memory (ROM) memory, an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

Execution of the instructions causes the processor to perform a method of sonicating a target volume. The method comprises the step of receiving a treatment plan specifying a target volume within the imaging volume. The method further comprises the step of acquiring magnetic resonance image data using the treatment apparatus. Magnetic resonance image data is data which is used to construct an image which details anatomical information about the region of the subject located within the imaging volume. Many magnetic resonance imaging systems will acquire magnetic resonance imaging data which determines the density of hydrogen atoms within the imaging volume. Hydrogen atoms are also referred to in the art as protons because a hydrogen atom only has a single proton. The method further comprises the step of registering the magnetic resonance image data to the treatment plan.

The treatment plan may comprise medical images of the subject, it may comprise anatomical atlas images and/or it may contain information about the location of anatomical landmarks with respect to their location to the image which is able to be constructed from the magnetic resonance imaging data. The registration of the magnetic resonance image data may comprise constructing one or more images or three-dimensional models of the imaging volume in the magnetic resonance imaging data. Once this has been completed these images or models may be used to determine the location of anatomical landmarks. This may be done using specific algorithms or analyzing the images or models or may also be done by fitting two or three-dimensional models to the images or models. For instance anatomical landmarks may be identified using edge detection algorithms such as a Sobel algorithm and using these identified edges to identify the anatomical landmark. Alternatively shape constrained deformable models may also be used to identify anatomical landmarks.

Registering the magnetic resonance imaging data to the treatment plan creates a link between the anatomy as identified in the treatment plan and the anatomy of the subject as the subject is currently positioned with respect to the magnetic resonance imaging system and to the high-intensity focused ultrasound system. This registration allows a modification of the treatment plan to account for the current position of the subject.

The method further comprises the step of modifying the treatment plan using the registration of the magnetic resonance imaging data to the treatment plan. The method further comprises the step of controlling the high-intensity focused ultrasound system by executing the treatment plan. In this step the high-intensity focused ultrasound system is used to sonicate one or more sonication volumes of the subject. The sonication volume is moved around within the subject to sonicate or heat the target volume according to the treatment plan. The method further comprises the step of acquiring magnetic resonance thermometry data repeatedly during execution of the treatment plan. Acquiring the magnetic resonance thermometry data repeatedly allows the determination of the temperature within the imaging volume as a function of time. The method further comprises the step of modifying the treatment plan using the repeatedly acquired magnetic resonance thermometry data. The step of modifying the treatment plan using the repeatedly acquired magnetic resonance thermometry data may include using the magnetic resonance thermometry data to calculate temperature map and then using the temperature map for modifying the treatment plan. This embodiment is advantageous because a treatment plan for the subject is received and then the magnetic resonance imaging system is used to adjust the plan to conform to the patient's current position and anatomy. This embodiment is also advantageous because the magnetic resonance thermometry data may be used to modify or fine tune the treatment plan.

In another embodiment the method further comprises updating the magnetic resonance imaging data repeatedly during execution of the treatment plan. Updating the magnetic resonance imaging data repeatedly may have several different interpretations. For instance this may include acquiring new magnetic resonance imaging data and replacing it. In this case the magnetic resonance imaging data could be re-registered to the existing treatment plan and used for modifying it. Updating the magnetic resonance imaging data may also include making a measurement of a smaller region such as a navigator scan. In a navigator scan the monitoring of a small region of the subject may be used to determine the location of the anatomy due to some periodic motion, for instance a navigator may be used to monitor the position of a subject's diaphragm. In this case the phase of the breathing may be correlated to the treatment plan and adjusted for. Similar navigator measurements may also be made for the heart. The method further comprises modifying the treatment plan using the repeatedly updated magnetic resonance imaging data. This embodiment is advantageous because the treatment plan is updated for motion of the subject.

In another embodiment the step of modifying the treatment plan using the magnetic resonance image data comprises modeling the transmission of ultrasound from the high-intensity focused ultrasound transducer to the target volume using the repeatedly updated magnetic resonance imaging data. In this embodiment the magnetic resonance imaging data is used for modeling the transmission of ultrasound of the high-intensity focused ultrasound transducer to the target volume. At the same time that this modeling occurs, a measurement of the temperature of all or part of the imaging volume is made using the magnetic resonance imaging system. The combination of modeling and measurement of the actual temperature allows an accurate determination of the sonication of the sonication volume. This leads to more accurate sonication of the target volume and to a greater degree of control of temperature of not only the target volume but also of the tissue surrounding the target volume. This reduces the risk of injury to the subject during execution of the treatment plan.

In another embodiment the computer readable storage medium further comprise instructions for implementing a stochastic simulation module for modeling the transmission of ultrasound from the high-intensity focused ultrasound transducer to the target volume using the repeatedly updated magnetic resonance imaging data. The stochastic simulation module comprises instructions for using a stochastic simulation to model the transmission of ultrasound from the high-intensity focused ultrasound transducer to a target volume by calculating approximate predictions which improve with an increasing simulation time. This embodiment is advantageous because a simulation of the desired accuracy can be made by using simulation time. For instance a short simulation may be done which produces rough estimates of changes in the treatment plan and its effect on the subject.

In another embodiment the computer readable storage medium further comprise instructions for implementing a fast approximation simulation module for modeling the transmission of ultrasound from the high-intensity focused ultrasound transducer to the target volume using the repeatedly updated magnetic resonance imaging data. The fast approximation simulation module comprises instructions for modeling the transmission of ultrasound from the high-intensity focused ultrasound transducer to the target volume by approximating the acoustic path as a stack of planer interfaces.

In another embodiment the computer readable storage medium further comprise instructions for implementing an acoustic field estimation module for modeling the transmission of ultrasound from the high-intensity focused ultrasound transducer to the target volume using the repeatedly updated magnetic resonance imaging data. The acoustic field estimation module comprises instructions for estimating the acoustic field for a subset of transducer elements of a high-intensity focused ultrasound transducer.

In another embodiment the method further comprises the step of creating the treatment plan using medical image data. Medical image data is defined herein as two or three dimensional data that has been acquired using a medical imaging scanner. A medical imaging scanner is defined herein as an apparatus adapted for acquiring information about the physical structure of a patient and construct sets of two dimensional or three dimensional medical image data. Medical image data can be used to construct visualizations which are useful for diagnosis by a physician. As an example, medical image data may be acquired by a positron emission tomography system, an X-ray computer tomography system, a magnetic resonance imaging system, and an ultrasound imaging system. This embodiment is advantageous because the medical image data is descriptive of the anatomy of the subject and this may be used to create a detailed treatment plan.

In another embodiment the step of creating the treatment plan comprises receiving planning data from a user interface.

For instance the medical image data may be displayed on a display. The display may for instance be a graphical user interface on a computer monitor. An operator, physician or other healthcare provider may use the user interface to design the treatment plan.

In another aspect the invention provides for a computer program product containing machine executable instructions for execution by a controller of a therapeutic apparatus. The therapeutic apparatus comprises a high-intensity focused ultrasound system for sonicating a sonication volume of a subject. The therapeutic apparatus further comprises a magnetic resonance imaging system for acquiring magnetic resonance imaging data and for acquiring magnetic resonance thermometry data from nuclei of the subject located within the imaging volume. The sonication volume is within the imaging volume.

The controller is adapted for controlling the therapeutic apparatus. The controller is adapted for receiving a treatment plan specifying a target volume within the imaging volume. The treatment plan comprises instructions for controlling the operation of the high-intensity focused ultrasound system. The machine executable instructions comprise instructions for sonicating the target volume with the high-intensity focused ultrasound system by executing the treatment plan. The machine executable instructions further comprise instructions for acquiring magnetic resonance thermometry data using the magnetic resonance imaging system during execution of the treatment plan. The machine executable instructions further comprise instructions for modifying the treatment plan during execution of the treatment plan using the magnetic resonance thermometry data.

In another aspect the invention also provides for a computer-readable storage medium as was described above in an embodiment of the invention. It is understood that a reference to a computer-readable storage medium is equally applicable to multiple computer-readable storage mediums. Code for a program may be distributed amongst several distinct computer-readable storage mediums.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
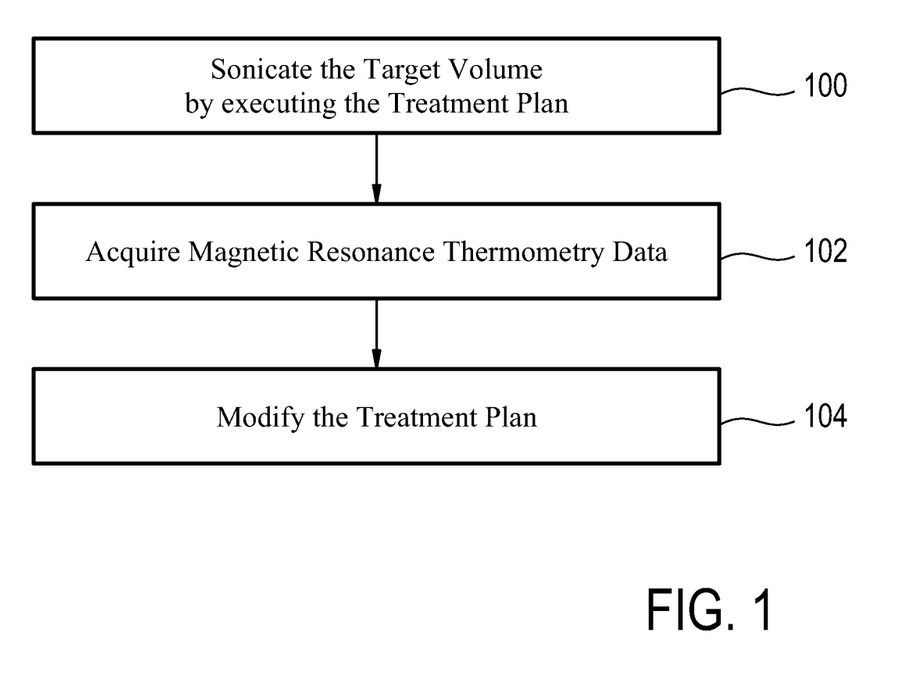
FIG. 1 shows an embodiment of a method according to the invention.

FIG. 1 shows an embodiment of a method according to the invention. In step 100 a target volume is sonicated by executing a treatment plan. In step 102 magnetic resonance thermometry data is acquired. Finally in step 104 the treatment plan is modified using the magnetic resonance thermometry data.

Figure 2:
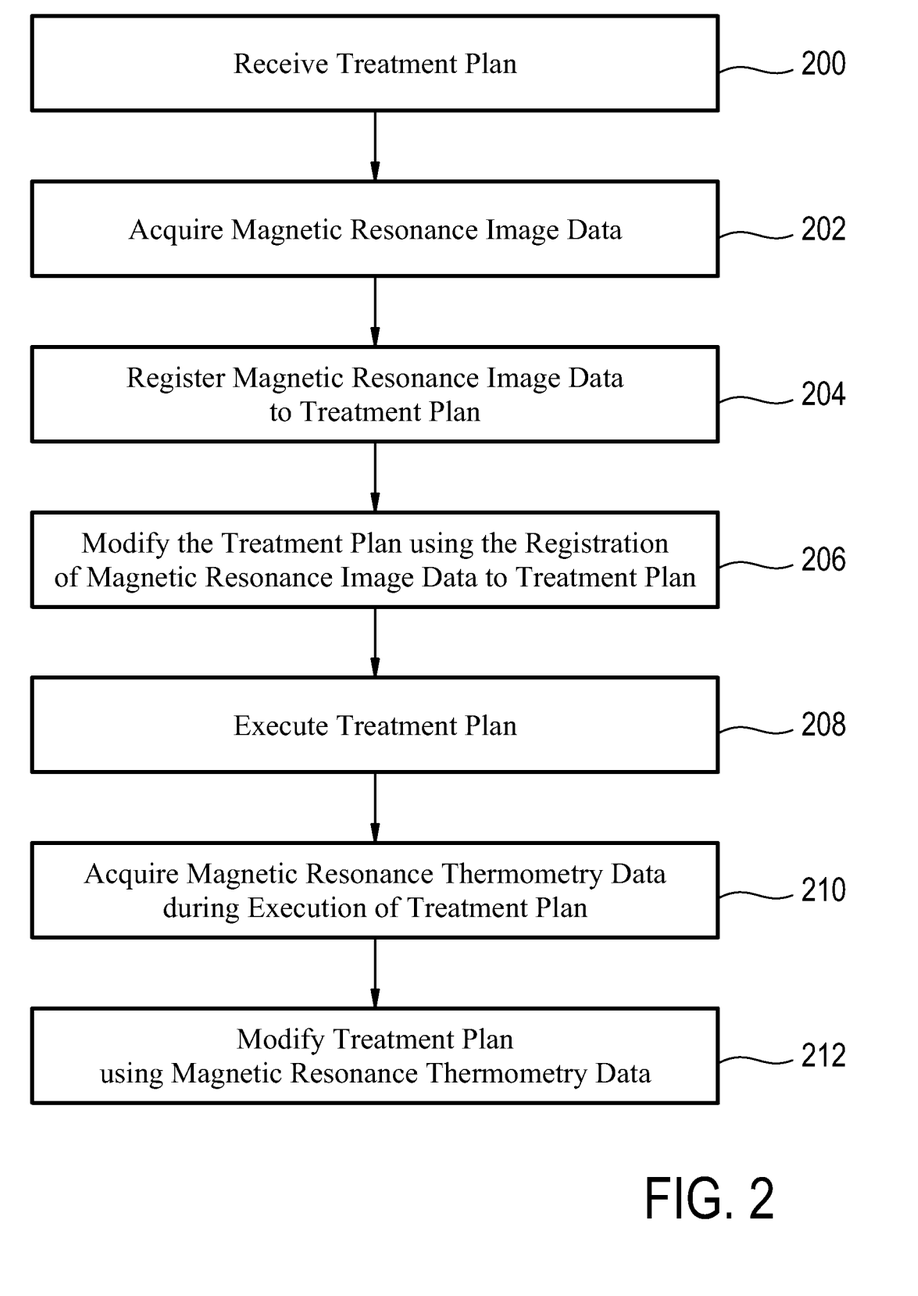
FIG. 2 shows a further embodiment of a method according to the invention.

FIG. 2 shows a further embodiment of a method according to the invention. In step 200 a treatment plan is received. In step 202 magnetic resonance image data is acquired. In step 204 the magnetic resonance imaging data is registered to the treatment plan. The registration is a correlation between the anatomy as measured by the magnetic resonance imaging data is correlated to anatomy recorded in the treatment plan. In step 206 the treatment plan is modified using the registration of the magnetic resonance image data to the treatment plan. The treatment plan is updated for the current anatomy of the subject. The subject may be in a different position and internal organs may also be located in a different position from when the treatment plan was made. In step 208 the treatment plan is executed.

In step 210 magnetic resonance thermometry data is acquired during execution of the treatment plan. In step 212 the treatment plan is modified using the magnetic resonance thermometry data.

Figure 3:
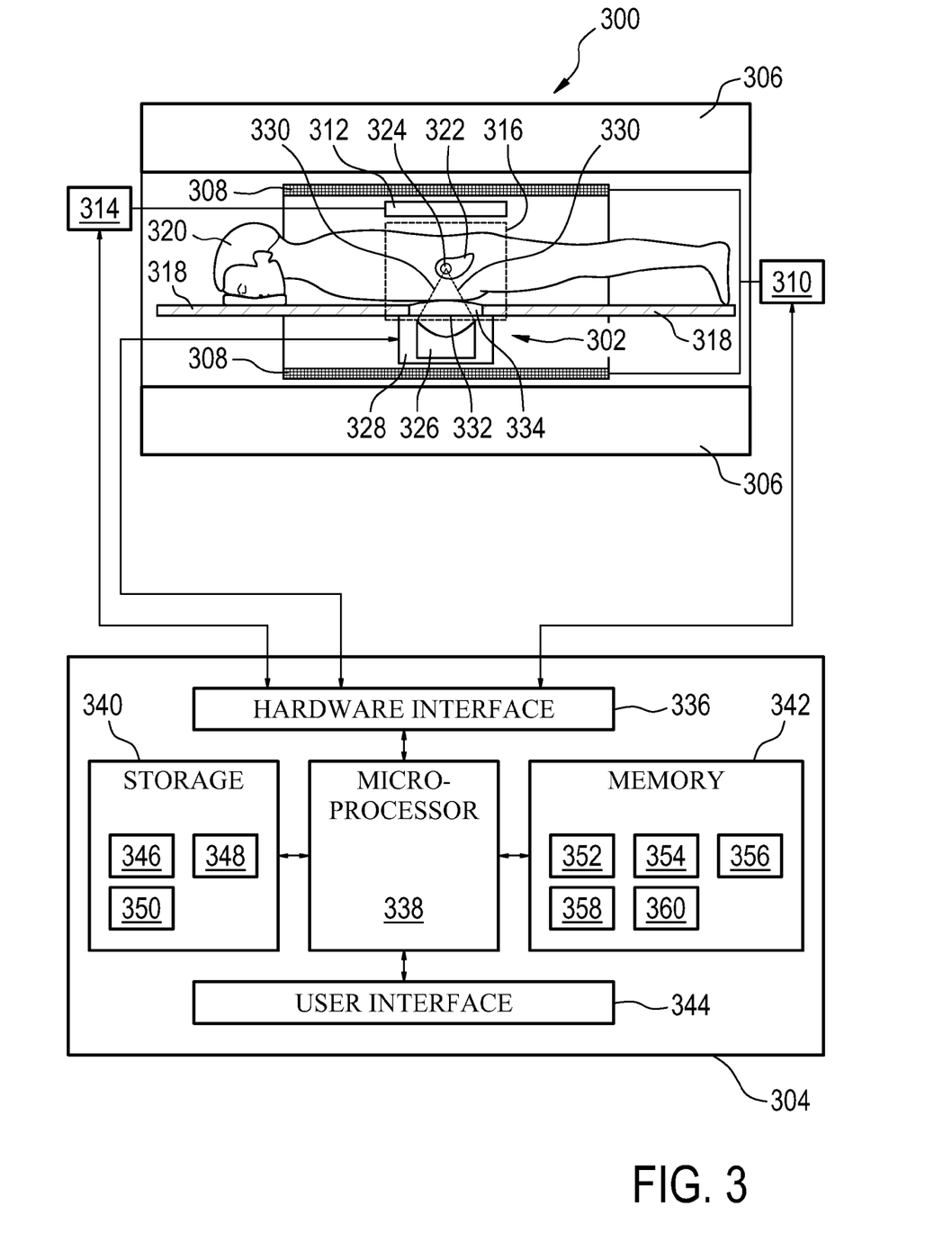
FIG. 3 shows a functional diagram which illustrates a therapeutic apparatus according to an embodiment of the invention.

FIG. 3 shows a functional diagram which illustrates an embodiment of a therapeutic apparatus according to the invention. The therapeutic apparatus is shown as comprising of a magnetic resonance imaging system 300, a high-intensity focused ultrasound system 302 and a computing device 304. The magnetic resonance imaging system 300 comprises a magnet 306. The magnetic resonance imaging system 300 also comprises a magnetic field gradient coil 308. The magnetic field gradient coil 308 is used for spatially encoding the spin of nuclei located within the imaging volume 316. The magnetic field gradient coil 308 is connected to a magnetic field gradient coil power supply 310. The magnetic field gradient power supply 310 supplies electrical current for powering the magnetic field gradient coil 308. When current is driven through the magnetic field gradient coil 308 the coils may be used to generate magnetic field gradients within the imaging volume 316. The magnetic field gradient coil may comprise more than one magnetic field gradient coil. For instance it is typical to have three different sets of magnetic field gradient coils for performing the spatial encoding.

Within the bore of the magnet 306 there is also a radio frequency transceiver coil. The radio frequency transceiver coil 312 is connected to a radio frequency transceiver 314. The radio frequency transceiver 314 is used to provide radio frequency electrical power for driving the radio frequency transceiver coil 312 and also for receiving radio frequency emissions from the spins of nuclei within an imaging volume 316. The radio frequency transceiver coil 312 may be used to manipulate the orientation of spins of nuclei within the imaging volume 316. In other embodiments, the transceiver coil 312 may be separate transmission and receive coils. Similarly, the transceiver 314 may be a separate transmitter and a separate receiver in other embodiments.

Located within the bore of the magnet is a subject support 318. On top of the subject support 318 is shown a subject 320. Within the subject 320 is a target volume 322. Shown within the target volume 322 is a sonication volume 324. The sonication volume is a region where ultrasonic energy from an ultrasonic transducer 326 has been focused.

The high-intensity focused ultrasound system comprises an ultrasonic transducer 326. The ultrasonic transducer 326 is located within a fluid-filled chamber 328. The fluid within the fluid-filled chamber 328 is a fluid which is adapted for transmitting ultrasonic energy. For instance the fluid may be degassed water. Not shown within this diagram is a power supply for powering the ultrasonic transducer and also a mechanical system for mechanically moving the position of the ultrasonic transducer 326. The lines marked 330 show the path of the ultrasound 330 from the ultrasonic transducer 326 to the sonication volume 324.

In this figure it can be seen that the ultrasound first passes through the fluid-filled chamber 328 and then through an ultrasonic window 332 which seals the fluid-filled chamber 328. The ultrasonic window 332 is typically a thin film like material which is adapted for transmitting ultrasound. Mylar is typically used as an ultrasonic window. In this embodiment there is an orifice within the subject support 318 which is filled by a gel pad 334. A gel pad is a pad which is adapted for transmitting ultrasonic energy. The gel pad 334 is used to form an ultrasonic conducting path between the ultrasonic window 332 and the subject 320. In other embodiments other ultrasonic conducting medium such as an ultrasonic gel or water may be used to assist in forming an interface between the subject 320 and the ultrasonic window 332.

The computing device 304 is adapted for controlling the therapeutic apparatus. The computing device 304 has a hardware interface 336 which is connected to the magnetic field gradient power supply 310, the radio frequency transceiver 314 and the high-intensity focused ultrasound system 302. The hardware interface 336 may be a single hardware interface or it may be a collection of hardware interfaces which are adapted for communicating with each of these components. The hardware interface 336 is connected to a microprocessor 338. The microprocessor 338 is a processor adapted for executing machine executable instructions. The microprocessor is also connected to computer storage 340.

As was mentioned before, the computer storage is a type of computer readable storage medium. Instructions may be loaded from the computer storage and performed by the microprocessor 338. Examples of computer storage are a hard drive, a thumb drive, a floppy disk and a solid state hard drive. Microprocessor 338 is also connected to computer memory 342. The computer memory 342 is memory which is accessible to the microprocessor 338. The computer memory 342 is also an embodiment of a computer readable storage medium. The computer memory may be, but is not limited to: RAM memory, a cache, and a register file. The microprocessor 338 is also connected to a user interface 344. The user interface may be adapted for displaying information to an operator or user. The user interface may also be adapted for receiving instructions or control sequences from an operator.

Located within the computer storage 340 is a treatment plan. Also located within the computer storage 340 is stored magnetic resonance image data 348. Also located within computer storage 340 is magnetic resonance thermometry data. Located within the computer memory 342 is a magnetic resonance imaging system control module 352 which contains instructions for controlling the operation of the magnetic resonance imaging system. Also located within the computer memory 342 is a magnetic resonance data reconstruction module 354 which may contain instructions for reconstructing magnetic resonance imaging data into magnetic resonance images and/or reconstructing magnetic resonance thermometry data into magnetic resonance maps.

Magnetic resonance images are images which may be displayed and convey anatomical information. Magnetic resonance thermometry maps are maps which show the spatial variation of temperature as measured by the magnetic resonance imaging system. A magnetic resonance thermometry map may be superimposed over a magnetic resonance image or other anatomical information to be used as a reference for indicating which anatomical region has which temperature.

The computer memory 342 further comprises an ultrasound modeling module 358. The ultrasound modeling module 358 comprises instructions for modeling the transmission of ultrasound energy from the ultrasonic transducer 326 to the sonication volume 324. The ultrasound modeling module 358 may be, but is not limited to, a stochastic simulation module, a fast approximation simulation module, or an acoustic field estimation module.

The stochastic simulation module may be implemented as a stochastic simulation which is used to quickly form a gradually improving estimate of the acoustic field. The approach is commonly used in optical lens system simulations. Discrete acoustic rays are randomly emitted from the transducer elements, and ray tracing techniques are used to model their propagation towards the volume of interest. The obtained estimate is rough at first, and improves with time when more rays are simulated.

The fast approximation simulation module may be implemented using an algorithm for approximating the acoustic path. In this algorithm, the acoustic path is approximated as consisting of a stack of homogeneous materials constrained between planar interfaces. Such special geometries are common in the field of diffractive optics, and computationally superior algorithms utilizing Fast Fourier Transform have been developed. Maximal simulation speed is achieved if the same geometry model is used for all transducer elements. For improved accuracy, the transducer elements can be partitioned into element groups, each having their own approximation of the geometry.

The acoustic field estimation module may be implemented using an algorithm which estimates the acoustic field. In this algorithm, the acoustic field is first estimated from a small subset of the transducer elements, and more elements are gradually included to improve the estimate. The elements are chosen fairly evenly distributed on the transducer surface, such that the intermediate intensity distribution is representative of the final distribution for all transducer elements. The simulation may be interrupted once the desired accuracy is obtained. The phase resonance of the simulated elements can be estimated using this approach, and thus also the focus quality.

The computer memory 342 further comprises a treatment plan modification module 360. The treatment plan modification module comprises machine executable instructions for performing the modification of the treatment plan using the magnetic resonance thermometry data and/or the magnetic resonance image data.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored and/or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

List Of Reference Numerals

300 magnetic resonance imaging system

302 high intensity focused ultrasound system 304 computing device
306 magnet
308 magnetic field gradient coil
310 magnetic field gradient coil power supply
312 radio frequency transceiver coil
314 radio frequency transceiver
316 imaging volume
318 subject support
320 subject
322 target volume
324 sonication volume
326 ultrasonic transducer
328 fluid filled chamber
330 path of ultrasound
332 ultrasonic window
334 gel pad
336 hardware interface
338 microprocessor
340 computer storage
342 computer memory
344 user interface
346 treatment plan
348 magnetic resonance image data
350 magnetic resonance thermometry data
352 magnetic resonance imaging system control module
354 magnetic resonance data reconstruction module
356 high intensity focused ultrasound system control module
358 ultrasound modeling module
360 treatment plan modification module

The invention claimed is:

1. A therapeutic apparatus comprising:
a high intensity focused ultrasound system for sonicating a sonication volume of a subject, the high intensity focused ultrasound system including an ultrasonic transducer located external to the subject within a fluid-filled chamber;
a magnetic resonance imaging system for acquiring magnetic resonance thermometry data from nuclei of the subject located within an imaging volume, wherein the sonication volume is within the imaging volume; and
a controller for controlling the therapeutic apparatus, wherein the controller is configured for:
receiving a treatment plan specifying a target volume within the imaging volume, wherein the treatment plan comprises instructions for controlling the operation of the high intensity focused ultrasound system;
sonicating the target volume using the high intensity focused ultrasound system by executing the treatment plan;
repeatedly acquiring magnetic resonance thermometry data using the magnetic resonance imaging system during execution of the treatment plan;
modifying the treatment plan during execution of the treatment plan using the magnetic resonance thermometry data;
acquiring magnetic resonance image data using the magnetic resonance imaging system, the magnetic resonance image data conveying anatomical information;
repeatedly updating the magnetic resonance image data during execution of the treatment plan; and
modifying the treatment plan using the repeatedly updated magnetic resonance image data by at least: modeling the transmission of ultrasound from a high intensity focused ultrasound transducer of the high intensity focused ultrasound system to the target volume using the repeatedly updated magnetic resonance image data, and using one or more of a stochastic simulation, a fast approximation simulation and an acoustic field estimation.

2. The therapeutic apparatus of claim 1, wherein modification of the treatment plan occurs during sonication of the target volume.

3. The therapeutic apparatus of claim 1, further comprising:
a stochastic simulation module for modeling the transmission of ultrasound from the high intensity focused ultrasound transducer to the target volume using the repeatedly updated magnetic resonance image data,
the stochastic simulation module using a stochastic simulation to model the transmission of ultrasound from the high intensity focused ultrasound transducer to the target volume by calculating approximate predictions which improve with an increasing simulation time.

4. The therapeutic apparatus of claim 3, wherein the stochastic simulation includes:
randomly emitting discreet acoustic rays from simulated transducer elements; and
ray tracing the propagation of the acoustic rays towards the target volume.

5. The therapeutic apparatus of claim 1, further comprising:
a fast approximation simulation module for modeling the transmission of ultrasound from the high intensity focused ultrasound transducer to the target volume using the repeatedly updated magnetic resonance image data,
the fast approximation simulation module modeling the transmission of ultrasound from the high intensity focused ultrasound transducer to target volume by approximating the acoustic path as a stack of planar interfaces.

6. The therapeutic apparatus of claim 1, further comprising:
an acoustic field estimation module for modeling the transmission of ultrasound from the high intensity focused ultrasound transducer to the target volume using the repeatedly updated magnetic resonance image data,
the acoustic field estimation module estimating the acoustic field for a subset of transducer elements of a high intensity focused ultrasound transducer.

7. The therapeutic apparatus of claim 6, wherein the estimating includes:
gradually adding transducer elements to improve accuracy.

8. The therapeutic apparatus of claim 1, wherein the controller is further configured for:
creating the treatment plan using medical image data.

9. The therapeutic apparatus of claim 8, wherein the controller is further adapted for creating the treatment plan using medical image data by at least:
receiving planning data from a user interface.

10. A non-transitory computer program product containing machine executable instructions for execution by a controller of a therapeutic apparatus,
wherein the machine executable instructions comprise instructions for:
receiving a treatment plan specifying a target volume within an imaging volume of a magnetic resonance imaging system, the treatment plan comprising instructions for controlling the operation of a high intensity focused ultrasound system;
controlling the high intensity focused ultrasound system to execute the treatment plan by sonicating the target volume;

acquiring magnetic resonance thermometry data from the magnetic resonance imaging system during execution of the treatment plan;
modifying the treatment plan during execution of the treatment plan using the magnetic resonance thermometry data;
acquiring magnetic resonance image data from the magnetic resonance imaging system;
repeatedly updating the magnetic resonance image data during execution of the treatment plan; and
modifying the treatment plan using the repeatedly updated magnetic resonance image data by at least:
  modeling the transmission of ultrasound from a high intensity focused ultrasound transducer of the high intensity focused ultrasound system to the target volume using the repeatedly updated magnetic resonance image data, and using one or more of a stochastic simulation, a fast approximation simulation and an acoustic field estimation.

11. The non-transitory computer program product of claim 10, wherein the machine executable instructions further comprise instructions for:
  modifying the treatment plan during sonication of the target volume.

12. The non-transitory computer program product of claim 10, wherein the machine executable instructions further comprise instructions for:
  creating the treatment plan using medical image data.

13. The non-transitory computer program product of claim 10, wherein the high intensity focused ultrasound system includes an ultrasonic transducer located external to the subject within a fluid-filled chamber.

14. The non-transitory computer program product of claim 10, wherein the magnetic resonance image data conveys anatomical information.

15. A method of sonicating a target volume, comprising:
receiving a treatment plan specifying the target volume within an imaging volume;
acquiring magnetic resonance image data using a magnetic resonance imaging system;
registering the magnetic resonance image data to the treatment plan;
modifying the treatment plan using the registration of the magnetic resonance image data to the treatment plan;
controlling a high intensity focused ultrasound system by executing the treatment plan;
acquiring magnetic resonance thermometry data repeatedly during execution of the treatment plan;
modifying the treatment plan using the repeatedly acquired magnetic resonance thermometry data;
updating the magnetic resonance image data repeatedly during execution of the treatment plan; and
modifying the treatment plan using the repeatedly updated magnetic resonance image data by at least: modeling the transmission of ultrasound from a high intensity focused ultrasound transducer of the high intensity focused ultrasound system to the target volume using the repeatedly updated magnetic resonance image data, and using one or more of a stochastic simulation, a fast approximation simulation and an acoustic field estimation.

16. The method of claim 15, further comprising:
creating the treatment plan using medical image data.

17. The method of claim 16, wherein the step of creating the treatment plan comprises:
receiving planning data from a user interface.

18. The method of claim 15, wherein the high intensity focused ultrasound system includes an ultrasonic transducer located external to the subject within a fluid-filled chamber.

* * * * *